US009504528B2

(12) United States Patent
Ivinson et al.

(10) Patent No.: US 9,504,528 B2
(45) Date of Patent: Nov. 29, 2016

(54) BIDIRECTIONAL RAMPED DISPOSABLE TORQUE LIMITING DEVICE

(71) Applicant: ECA MEDICAL INSTRUMENTS, Newbury Park, CA (US)

(72) Inventors: David Ivinson, Camarillo, CA (US); John Nino, Simi Valley, CA (US); Gary Norsworthy, Reseda, CA (US)

(73) Assignee: ECA Medical Instruments, Newbury Park, CA (US)

( * ) Notice: Subject to any disclaimer, the term of this patent is extended or adjusted under 35 U.S.C. 154(b) by 548 days.

(21) Appl. No.: 14/007,912

(22) PCT Filed: Nov. 20, 2012

(86) PCT No.: PCT/US2012/066090
§ 371 (c)(1),
(2) Date: Sep. 26, 2013

(87) PCT Pub. No.: WO2013/137942
PCT Pub. Date: Sep. 19, 2013

(65) Prior Publication Data
US 2014/0366691 A1    Dec. 18, 2014

Related U.S. Application Data

(60) Provisional application No. 61/610,405, filed on Mar. 13, 2012.

(51) Int. Cl.
*A61B 19/00* (2006.01)
*B25B 23/14* (2006.01)
*B25B 23/142* (2006.01)

(52) U.S. Cl.
CPC ............... *A61B 19/30* (2013.01); *A61B 90/03* (2016.02); *B25B 23/141* (2013.01); *B25B 23/1415* (2013.01); *B25B 23/1427* (2013.01); *A61B 2090/031* (2016.02); *Y10T 29/49826* (2015.01)

(58) Field of Classification Search
CPC  A61B 19/30; A61B 2019/301; A61B 19/00; A61B 2090/031; A61B 90/03; B25B 23/141; B25B 23/1415; B25B 23/1427; A61C 3/00; Y10T 29/49826
See application file for complete search history.

(56) References Cited

U.S. PATENT DOCUMENTS

| 2,561,136 A * | 7/1951 | Richardson | F16D 7/044 464/39 |
| 3,535,958 A * | 10/1970 | Larson | B25B 23/1427 81/475 |
| 2009/0255386 A1 * | 10/2009 | Liao | B25B 13/06 81/474 |

(Continued)

FOREIGN PATENT DOCUMENTS

| JP | 59-163466 | 11/1984 |
| JP | S59-163466 U | 11/1984 |

(Continued)

OTHER PUBLICATIONS

International Search Report and Written Opinion mailed Mar. 27, 2013, as received in the corresponding International Application No. PCT/US2012/066090.

*Primary Examiner* — Joseph J Hail
*Assistant Examiner* — Marc Carlson
(74) *Attorney, Agent, or Firm* — Baker & Hostetler LLP

(57) ABSTRACT

A bidirectional torque limiting driver with a handle, internal wall, movable head and a tool mounted thereon, with flexible torque limiting flex ramp(s) formed on said internal wall, whereby said ramps move under sufficient force to impart a predetermined torque to a tip is disclosed.

18 Claims, 6 Drawing Sheets

(56) References Cited

U.S. PATENT DOCUMENTS

| | | | |
|---|---|---|---|
| 2011/0056341 A1* | 3/2011 | Lai | B25B 13/06 81/475 |
| 2011/0094354 A1* | 4/2011 | Lai | B25B 13/06 81/475 |
| 2012/0227221 A1* | 9/2012 | Whitaker | A61M 39/1011 24/459 |
| 2015/0342693 A1* | 12/2015 | Ivinson | F16D 7/04 464/38 |

FOREIGN PATENT DOCUMENTS

| | | | |
|---|---|---|---|
| JP | 61-071375 | 5/1986 | |
| JP | S61-71375 U | 5/1986 | |
| JP | 2001 121444 | 5/2001 | |
| JP | 2001-121444 A | 5/2001 | |
| KR | 10 1998 0008465 | 4/1998 | |
| KR | 10-1998-0008465 A | 4/1998 | |
| WO | WO 2013081934 A1 * | 6/2013 | A61C 3/00 |

* cited by examiner

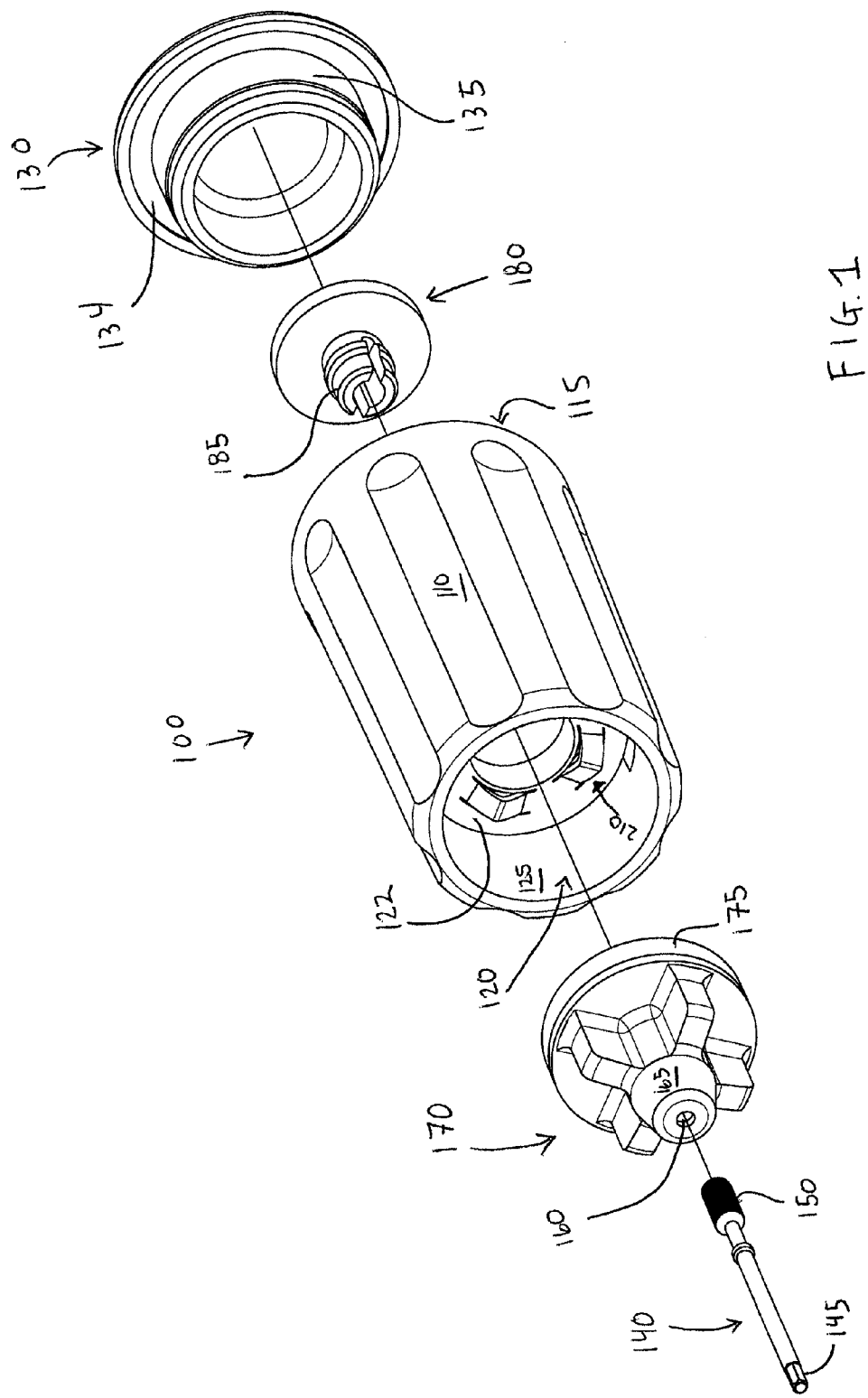

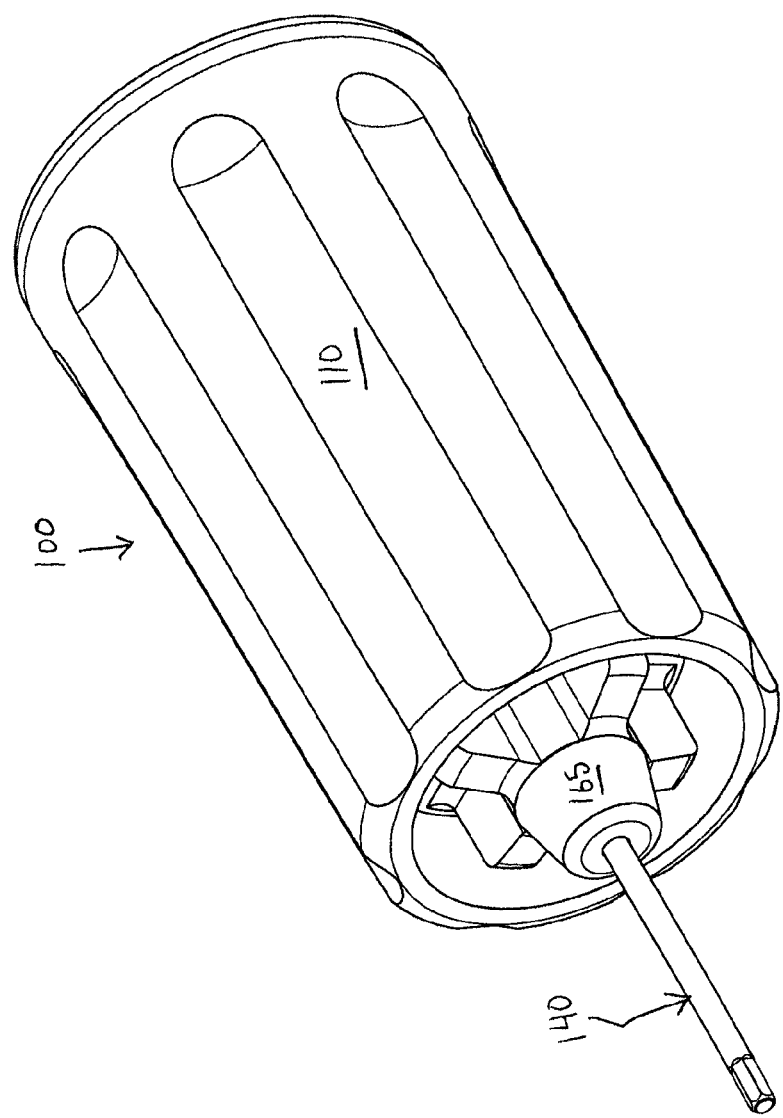

BIDIRECTIONAL RAMPED DISPOSABLE TORQUE LIMITING DEVICE

RELATED APPLICATIONS

The present application is a U.S. National Stage of International Application No. PCT/US2012/066090, filed Nov. 20, 2012, which claims the benefit of and priority to U.S. Provisional Application No. 61/610,405, filed Mar. 13, 2012, the entire disclosures of each of which are incorporated herein by reference in their entireties.

BACKGROUND

1. Field

This disclosure relates to a medical use driver tool and, in particular, to a bidirectional torque-limiting driver that disengages at a predefined torque limit, which provides for a predetermined number of uses.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely.

Disposable drivers are an easy to use and reliable alternative to the reusable drivers. Typically, each implant, for example, is packaged with a disposable driver designed to the implant's specifications. Once the driver has been used, it can be discarded. Thus, a surgeon can have complete confidence that the disposable driver, packaged with an implant, will impart the precise amount of torque.

DESCRIPTION

Torque is a measure of how much force acting on an object causes that object to rotate. In the case of a driver and a fastener, this measurement can be calculated mathematically in terms of the cross product of specific vectors:

$$T = r \times F$$

Where r is the vector representing the distance and direction from an axis of a fastener to a point where the force is applied and F is the force vector acting on the driver.

Torque has dimensions of force times distance and the SI unit of torque is the Newton meter (Nm). The joule, which is the SI unit for energy or work, is also defined as an Nm, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A simple torque limiting driver that will provide a predetermined number cycles at a nominal torque limit is disclosed.

In some exemplary implementations, the actuation to be in either the clockwise direction or the counterclockwise direction each having a torque setting of 15.0+3.0/−2.0 oz-in under no axial load. Maximum torque must remain under 20.0 oz-in under a measured axial load up to 5.0 lbs.

In some exemplary implementations, the actuation to be in either the clockwise direction or the counterclockwise direction, each having a torque setting of 15.0+3.0/−2.0 oz-in under no axial load. Maximum torque must remain under 20.0 oz-in under a measured axial load up to 5.0 lbs and there is about 15.0 degrees of minimum free play.

In some exemplary implementations, movable torque limiting flex ramps (TLFR) are formed on a wall bisecting said handle and locking stops are associated with movable nose cone.

In some exemplary implementations, movable torque limiting flex ramps (TLFR) are formed on a wall bisecting said handle and force heads associated with movable nose cone provide for actuation. Such actuation being the result of said TLFR acting as a living hinge, which moves in response to the force heads passing thereover at a predetermined force. TLFRs can flex in response to the passing of the force head(s) thereover.

In some instances, a nose cone may be molded in a plastic that has better lubricity properties than said handle. Driver will have about 15.0-degree minimum free play. Torque limiting driver is disposed of after one torque actuation.

In some exemplary implementations, there is disclosed a bidirectional torque limiting device comprising: a hollow body with and open proximal end and open distal end forming a handle; an internal wall bisecting said hollow body into a first and a second section on one side having at least one movable torque limiting flex ramp; a channel formed through said internal wall fluidly connecting said first and said second sections; a head surrounded by an annular wall which fits movably into said hollow body said head having a front side with a nose extended therefrom which has a tool mounted therein; said head having a backside which fits over said ramp further comprising; at least one force head; a peg extended therefrom having a catch; a plug with an extended latch of a size and shape to fit through said channel which mates with said peg's catch holding said head to said internal wall; whereby when rotated in either a forward or reverse direction the at least one force head will pass over said ramp and upon the application of sufficient torque allow passage of said force head, thereby biasing the device to a predetermined torque per ramp over movement.

In some exemplary implementations, there is disclosed a bidirectional torque limiting device comprising a hollow body with and open proximal end and open distal end forming a handle; an internal wall bisecting said hollow body into a first and a second section on one side having a at least one torque limiting flex ramp with a leading edge; a channel formed through said internal wall fluidly connecting said first and said second sections; a head surrounded by an annular wall which fits movably into said hollow body said head having a front side with a nose extended therefrom which has a tool mounted therein; said head having a backside which fits over said ramp further comprising; at least one force head; a peg extended therefrom having a catch; a plug with an extended latch of a size and shape to fit through said channel and mates with said peg's catch holding said head to said internal wall; and, whereby when rotated the at least one force head must apply a preselected amount of force to pass over said ramp, said ramp moving downward and allowing passage.

In some instances, a tool affixed to the nose of the bidirectional device is rotated by an amount of force corresponding to the force said stop is applying to said at least one ramp. In some instances, said ramp is a natural or living hinge, fixed to said internal wall having a bridge raised above two shoulders, each shoulder connected to said internal wall and said bridge will move downward under sufficient force or load when said force head passes thereover.

In some exemplary implementations, a method of applying a torque limiting actuation to a tip is disclosed whereby a user engages the tip of a driver to a fastener; applying the predetermined torque to depress or otherwise move said ramp downward via a rotational handle; tightening said fastener to the torque limit.

DRAWINGS

The above-mentioned features of the present disclosure will become more apparent with reference to the following description taken in conjunction with the accompanying drawings wherein like reference numerals denote like elements and in which:

FIG. 1 shows a front perspective component view of some aspects of an exemplary implementation of a single use torque limiting device;

FIG. 2 shows a front perspective view of some aspects of an exemplary implementation of a single use torque limiting device;

Figure 3B:
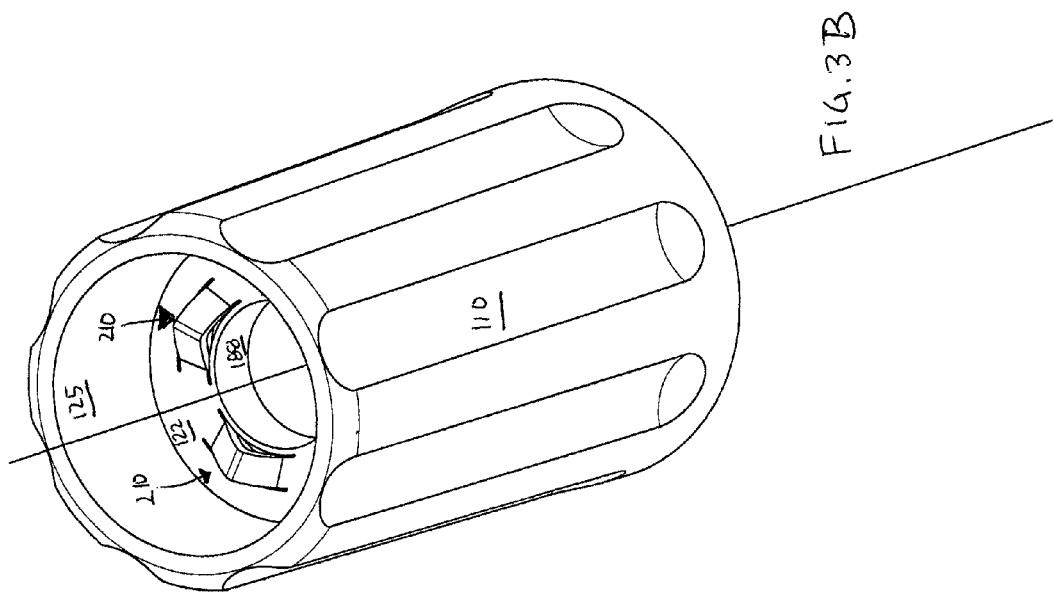
FIG. 3B shows a view of the front section of the handle component of FIGS. 1 and 2.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures are hereby incorporated by this reference as if fully set forth herein.

FURTHER DESCRIPTION

Referring to FIGS. 1-4B: In FIG. 1 there is shown an assembly view of a single use torque-limiting driver 100. The torque-limiting driver 100 has a generally hollow body 110 forming a handle with an open proximal end 115, an open distal end 120, and an internal circular wall 122 bisecting the handle into a first and a second section, which are shown as a front section 125 and a back section 220. Flexible ramps are formed on said wall. The illustration of said handle as a cylindrical device is not a limitation; said device may be other curved or geometric shapes such as ellipsoid, conical, square, polygonal and the like. Those of ordinary skill in the art will recognize that such design choices are all within the scope of this disclosure.

A circular cap 130 with a backside 132, a front side 134, and an annular wall 135 which extends from said front side 134, and of a size and shape to form a latch with said open proximal end 115 is shown in FIGS. 1-4.

A tool 140 with a tip 145 at its distal end and a fixed mount 150 at its proximal end is affixed at its proximal end into a mounting guide 160 located in a nose 165 extending from the front side of a head 170 component, the head acts as a support for the tool. The tip may be a drive for tightening fasteners or a cutting instrument. To effectively apply torque via the tip, the tip must be engaged. In some instances, said engagement will be with a fastener. In other instances, said engagement may be with material to be cut or resected. The head component is a movable element with an annular wall 175. The annular wall defines a diameter around the circular head that fits within said open distal end 120.

Although not fully visible in FIGS. 1 and 2, said head component 170 has a catch formed on its backside wherein a head plug 180 provides a latch 185 that fits through a plug channel through internal circular wall 122. In FIGS. 3 and 4, the plug channel 188 is shown.

The back side 177 of the head 170 is surrounded by an annular wall 175. The plug catch 178 is shown formed center aligned in a cylindrical peg 179 thereby providing a point whereby said head plug can movably attach said head to the internal circular wall 122 whereon the head may be rotated in furtherance of the disclosure. To effectuate a torque limited rotation as well as fixed reverse rotations (without torque limiting) a cooperative system is disclosed whereby a head piece attached to the bisecting internal circular wall via a head plug interacts with operational features formed on said internal wall 122.

Figure 3A:
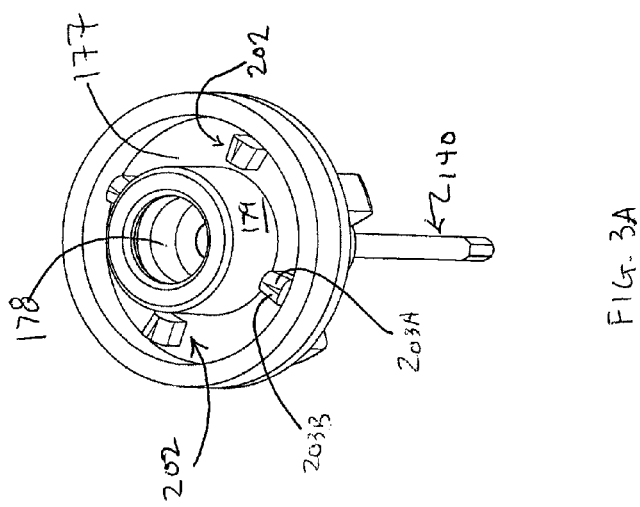
FIG. 3A shows a back view of the head component of FIGS. 1 and 2.

In FIGS. 3A and 3B, force heads 202 are shown extending from backside 177 of the head 170 component, which also acts as a support for the force heads. Said force heads 202, may have two opposing angled faces 203A and 203B formed on each side. Said angled faces are optional and not essential. During a rotation in a forward or backwards direction, the angled faces 203A and 203B move over torque limiting flex ramps (TLFR) 210 formed in said internal circular wall and do not catch. Rather, at least one force head will eventually encounter a torque limiting flex ramp (TLFR) 210. Said TLFR is raised from said internal wall 122 and limits the movement of the force head thereover—unless or until—sufficient force is applied during rotation to move the force head over the TLFR and overcome the TLFR's resistance to a downward movement, which allows passage of said force head.

A TLFR 210 is formed to require a predetermined amount of force, applied thereto via said force heads 202, to overcome the TLFR's impediment to rotation of the force head over said TLFR, which is movable under a predetermined force. When adequate force is applied by the force head 202 (or heads) the TLFR (or TLFRs) move in a direction downward from the force head (towards the internal wall 122) and generally axial in the device.

In some instances, a single force head 202 may be used. In other instances, multiple force heads may be used. In some instances, a single TLFR may be utilized. In some instances, the single TLFR is provided and it will encounter multiple force heads 202, each force head 202 reaching the TLFR as the tool 140 is rotated. In some instances, multiple TLFRs are provided. In a multiple TLFR configuration, a single force head 202 may be utilized. Said single force head must overcome the necessary resistance to force to pass over said TLFR during a partial rotation.

In a some multiple TLFR configurations, multiple force heads 202 are utilized. At least two of said multiple force heads may be oriented to each pass over a different TLFR during a partial rotation of the tool 140. In some instances, each of the multiple stops may be oriented to pass over a different TLFR during a partial rotation of the tool 140.

Figure 3C:
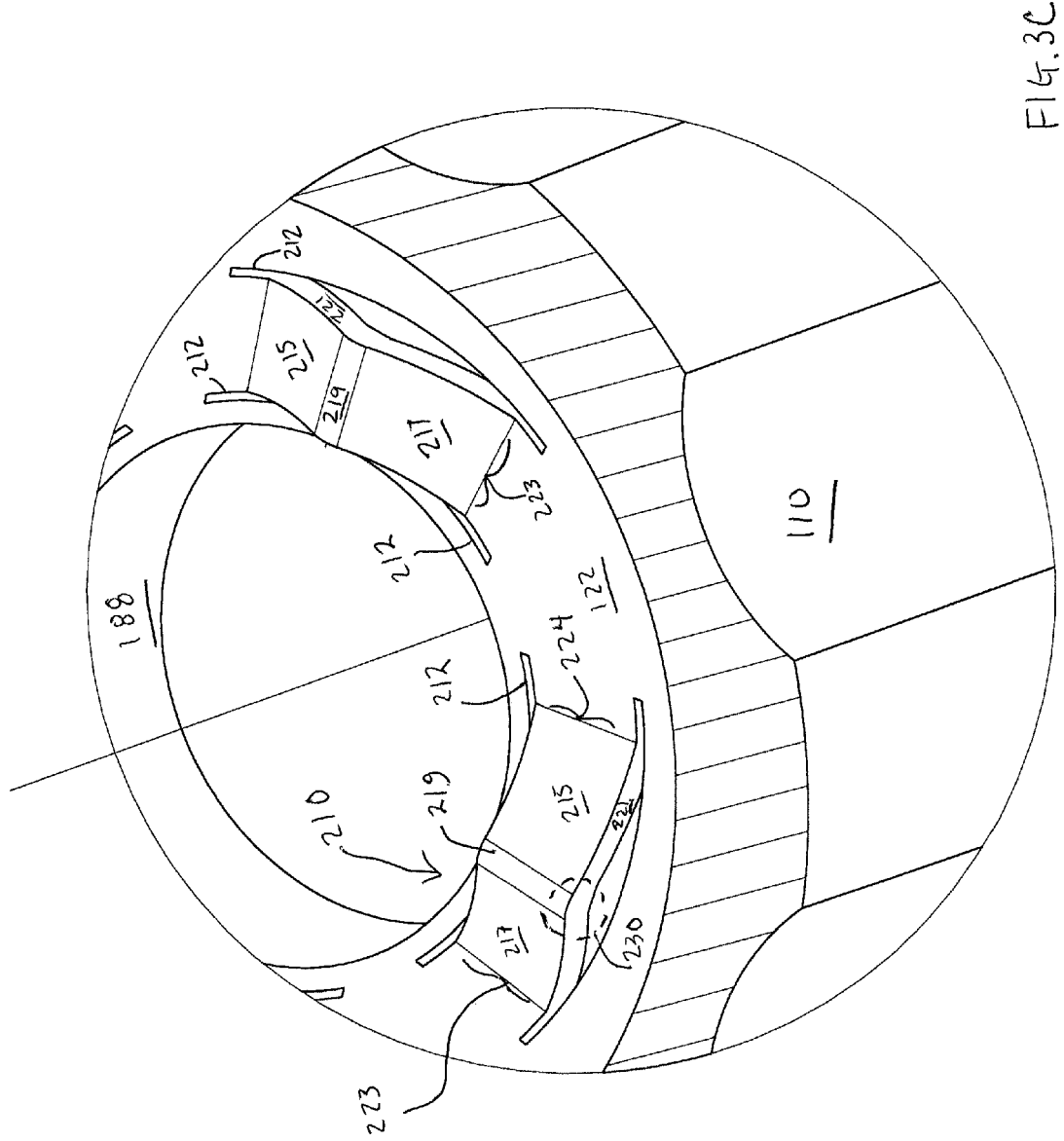
FIG. 3C shows a close-up view of aspects of at least one exemplary implementation of part of the internal wall and ramps for a bidirectional torque limiting device.
Figure 4A:
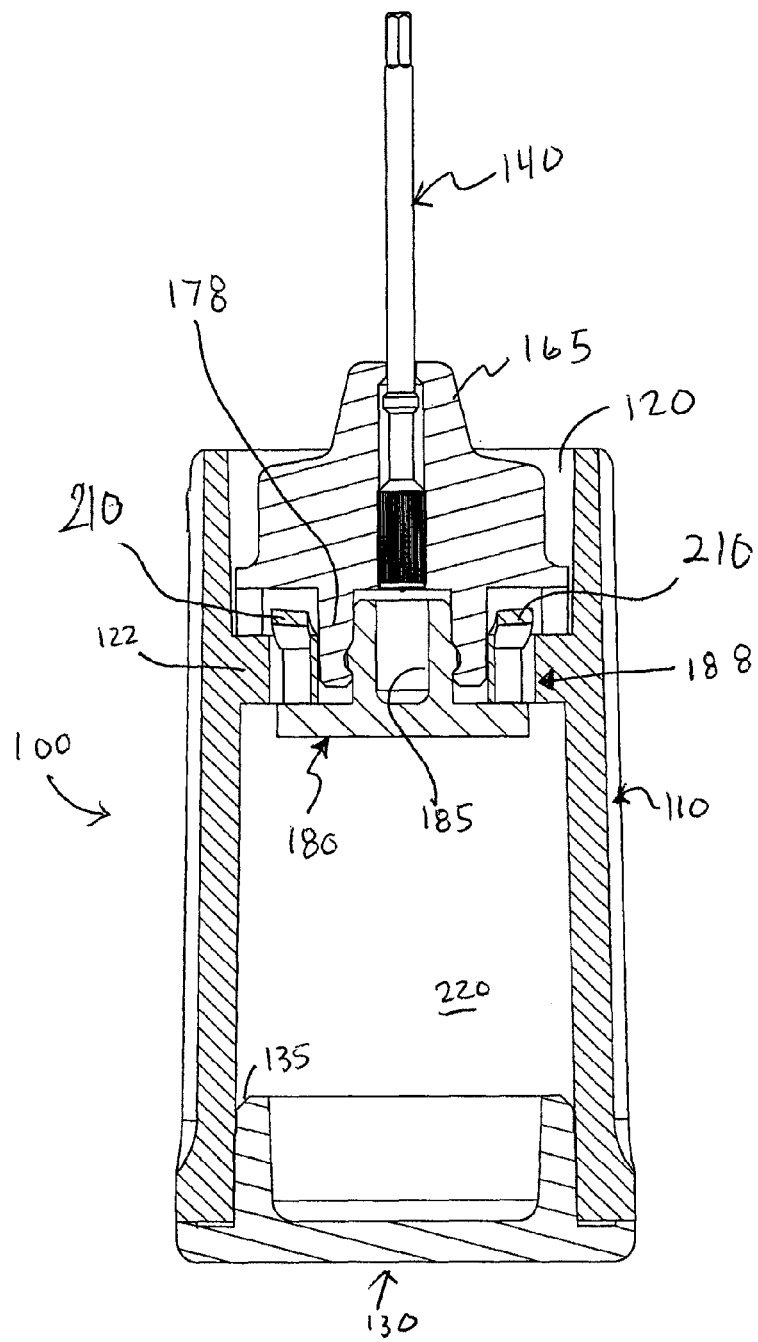
FIG. 4A shows a cut-away side view of some aspects of an exemplarily implementation of a single use torque limiting device.
Figure 4B:
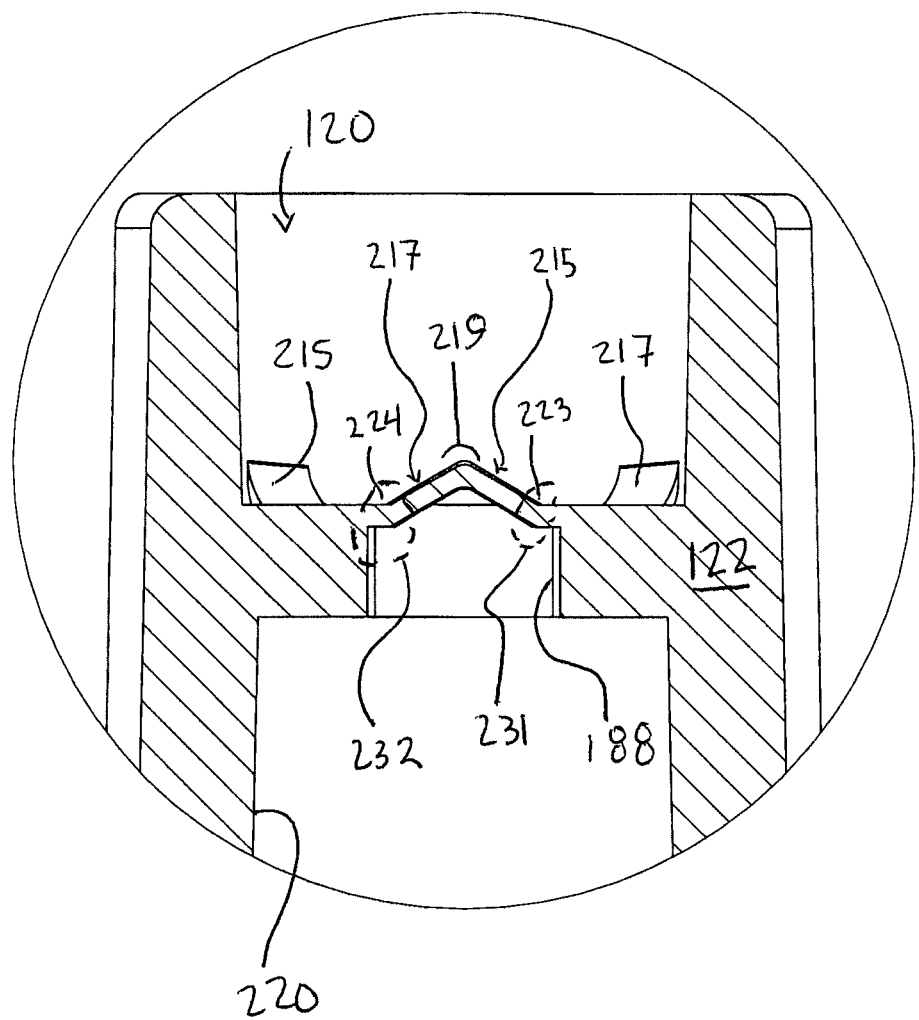
FIG. 4B shows a cut-away of the handle showing the ramps of FIG. 4A.

FIGS. 3C and 4B show partial blown up views of aspects of components comprising said force heads 202 and said TLFR 210. In some exemplary implementations, the TLFR 210 is a generally elongated member separated from said internal wall 122 by flex channels 212 which are guides or cutouts in the internal wall along the side edge of said TLFR. A TFLR may be thought of as a flexible bridge that has a first at rest position which is extended above the internal wall 122 and a second range of positions, when force is applied to the TFLR by force head, which moves the TLFR downward nearer to the internal wall. A TLFR is a two shoulder ramp fixture with a first shoulder 215 and a second shoulder 217; the shoulders meeting at a bridge 219. The shoulders each form a leading edge remote from the bridge. The TLFRs have a side edge 221 with a thickness. The TLFR bridge 219, when at rest, is above said internal wall 122 into the front section 120. At a first end 223 the TLFR is affixed to said internal wall 122 and at a second end 224, said TLFR is also affixed to said internal wall. In some instances, said flex channels 212 may extend beyond the point of affixation of said first and second ends to said internal wall. A control region 230 of the TLFR below the bridge 219 may be non-homogeneous in width or thickness from the rest of the TLFR to facilitate controlled movement of the TLFR corresponding to desired torque limits in response to force being applied. A second control region 231 at the connection of the first shoulder 215 with the internal wall 122 may be non-homogeneous in width or thickness from the rest of the TLFR to facilitate controlled movement of the TLFR corresponding to desired torque limits in response to force being applied. A third control region 232 at the connection of the second end 217 with the internal wall 122 may non-homogeneous in width or thickness from the rest of the TLFR (which includes regions of non-homogeneity) to facilitate controlled movement of the TLFR corresponding to desired torque limits in response to force being applied. Accordingly, a predefined amount of torque to flex the TLFR in response to movement of the force heads over the TLFR. The one or more control regions which may be non-homogeneous with the TLFR may be added to further set, or control, the torque limit of the TLFR. In other words to displace the TLFR the force heads must apply a predetermine amount of torque and a fixed tool tightening a fixture would tighten to the determined limit and then pass over the TLFR.

Those of ordinary skill in the art will recognize that several variables and design choices are involved in preselecting what amount of force must be applied to pass one or more stops over one or more TLFRs and achieve a nominal torque limit and that such variables and design choices are within the scope of this disclosure. Some such variables and design choices include but are not limited to the angle of the TLFR relative to the internal wall 122 the thickness of the TLFR. Also impacting the force requirements will be the lubricity of the materials, the hardness or softness of the materials, the memory of the materials, tensile strength, flexural strength, coefficient of friction, and the stiffness of the materials. A non-exclusive list of materials include polyetherimide (Ultem) material for all plastic components, polycarbonate (Lexan) material for plastic components, a Polyoxymethylene (Delrin) material for plastic components, and ABS (Acrylonitrile butadiene styrene) for plastic components. Other factors impacting force include how many force heads are passing over how many TLFRs at the same time. These variables are adjustable to meet a particular torque requirement.

Those of ordinary skill in the art will recognize that said force heads need not have angled faces to function; while it is preferred to achieve smooth operation and angled faces provide a larger surface to push over said TLFR.

FIG. 4A illustrates a cutaway assembled view of a bidirectional torque limiting. Head plug 180 via its extended latch 185 fits through the plug channel 188 of the internal circular wall 122 and mates with, to be held in, the plug catch 178 of said head. In this view, angled faces 203A and 203B are not visible. Behind the internal circular wall 122 is the back section 220 wherein fits the cap 130.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A bidirectional torque limiting device comprising:
   a hollow body (110) with and open proximal end (115) and open distal end (120) forming a handle;
   the hollow body including:
   an internal circular wall (122) separating the hollow body into a cylindrical front section (120) and a back section (220);
   at least one generally elongated torque limiting flex ramp (210) integrally formed on a first side of the internal circular wall;
   the elongated torque limiting flex ramp having a first ramped projection connected to the internal circular wall via first living hinge and a second ramped projection connected to the internal circular wall via a second living hinge, both at an incline relative to the internal circular wall and oriented to intersect at a raised peak bridging the two ramped surfaces;
      the raised peak spaced outward from the first side of the internal circular wall and comprising a third living hinge;
      a cavity formed in a second side the internal circular wall opposite the at least one generally elongated torque limiting flex ramp, the cavity generally sized to match both the ramped projections and the three living hinges of the at least one generally elongated torque limiting flex ramp;
      a plug channel (188) formed through the internal wall fluidly connecting the cylindrical front and the back sections;
   a tool head (170) having a front side with a nose (165) extended therefrom which has a tool (140) mounted therein;
   the tool head having an annular back side surface located between an outermost annular wall sized to movably fit inside the cylindrical front section of the hollow body and an innermost annular peg wall sized to fit inside the plug channel hole, the innermost annular peg having a catch feature formed thereon, the annular back side surface containing at least one bump stop (202) protruding therefrom;
   a head plug having a base sized to fit inside the back section of the hollow body but sized to be larger than the plug channel hole, the head plug having an extended latch protruding from the base that is sized and shaped to fit through the plug channel hole and fasten to the catch feature on the innermost annular peg to secure the outermost annular wall of the tool head to the first side of the internal circular wall and the base of the head plug to the second side of the internal circular wall;
   whereby when the handle is twisted relative to the tool, the at least one generally elongated torque limiting flex ramp on the hollow body will rotate toward the at least one bump stop on the tool head to an engagement point where the bump stop contacts the at least one generally elongated torque limiting flex ramp, at the engagement point additionally twisting of the handle will result in a twisting of the tool with a torque limited at level where the at least one bump stop deflects the first and second ramp portions into the cavity allowing the bump stop to rotate past the at least one generally elongated torque limiting flex ramp.

2. The device of claim 1 wherein when rotated, the at least one force head must apply a preselected amount of force to pass over said flex ramp by forcing the flex ramp downward and allowing passage of said force head.

3. The device of claim 1, wherein a tool affixed to the nose is rotated by an amount of force corresponding to the force said force head is applying to said at least one flex ramp.

4. The device of claim 1 wherein said raised peak is raised above two shoulders (217 and 215), each shoulder connected to said internal wall (122).

5. The device of claim 1 wherein said flex ramp is connected to the internal wall at the first and second ends (223 and 224).

6. The device of claim 4 further comprising flex channels (212) cutouts in the internal wall along the side edge (221) of said ramp.

7. The device of claim 4 further comprising one or more control regions (230, 231, and 232) formed as part of the flex ramp.

8. The device of claim 1 further comprising one or more control regions formed as part of the flex ramp.

9. The device of claim 7 wherein the one or more control regions are located below the raised peak, at the connection of the first shoulder (215) with the internal wall and at the connection of the second shoulder (217) with the internal wall.

10. The device of claim 8 wherein the one or more control regions are located below the raised peak, at the connection of a first shoulder (215) with the internal wall and at the connection of a second shoulder (217) with the internal wall.

11. The device of claim 9, wherein the one or more control regions are nonhomogeneous in one of width or thickness from the TLFR, whereby predefined amounts of torque are required to flex the TLFR in response to movement of the force heads over the TLFR.

12. The device of claim 10, wherein the one or more control regions are nonhomogeneous in one of width or thickness from the TLFR, whereby predefined amounts of torque are required to flex the TLFR in response to movement of the force heads over the TLFR.

13. A bidirectional torque limiting device comprising:
a hollow body (110) forming a handle;
an internal wall (122) separating the hollow body into a cylindrical first section and a second section;
integrally formed on one side of said wall an elongated torque limiting flex ramp having a first ramped projection connected to the internal circular wall via first living hinge and a second ramped projection connected to the internal circular wall via a second living hinge, both at an incline relative to the internal circular wall and oriented to intersect at a raised peak bridging the two ramped surfaces;
a channel formed through said internal wall fluidly connecting said first and said second sections;
a tool head surrounded by an annular wall which fits movably into said hollow body,
said tool head having a front side with a nose extended therefrom which has a tool mounted therein;
the tool head having an annular back side surface located between an outermost annular wall sized to movably fit inside the cylindrical front section of the hollow body and an innermost annular peg wall sized to fit inside the plug channel hole, the innermost annular peg having a catch feature formed thereon, the annular back side surface containing at least one bump stop protruding therefrom; and,
whereby, when the handle is twisted relative to the tool head, the at least one generally elongated torque limiting flex ramp on the hollow body will rotate toward the at least one bump stop on the tool head to an engagement point where the bump stop contacts the at least one generally elongated torque limiting flex ramp, at the engagement point additionally twisting of the handle will result in a twisting of the tool with a torque limited at a level whereby the at least one bump stop deflects the first and second ramp portions into the cavity allowing the bump stop to rotate past the at least one generally elongated torque limiting flex ramp.

14. The device of claim 13, wherein a tool affixed to the nose is rotated by an amount of force corresponding to the force said force head is applying to said at least one flex ramp.

15. The device of claim 13, wherein said flex ramp is connected to the internal wall at the first and second ends (223 and 224).

16. The device of claim 13 further comprising one or more control regions formed as part of the flex ramp.

17. The device of claim 16 wherein the control regions are located below the raised peak, at the connection of a first shoulder (215) with the internal wall and at the connection of a second shoulder (217) with the internal wall.

18. A method of setting a bidirectional torque limit, the method comprising:
forming one or more living hinge flex ramps (210) integrally in an internal circular wall, each flex ramp affixed at one end to the wall (122) and a first ramped projection connected to the internal circular wall via first living hinge and a second ramped projection connected to the internal circular wall via a second living hinge, both at an incline relative to the internal circular wall and oriented to intersect at a raised peak bridging the two ramped surfaces;
movably affixing a support (170) having one or more force head (202) thereon adjacent to said flex ramps;
attaching a tool (140) to said support (170); and,
whereby when the handle is twisted relative to the tool head, the at least one generally elongated torque limiting flex ramp on the hollow body will rotate toward the at least one bump stop on the tool head to an engagement point where the bump stop contacts the at least one generally elongated torque limiting flex ramp, at the engagement point additionally twisting of the handle will result in a twisting of the tool with a torque limited at a level whereby the at least one bump stop applies a predetermined amount of force to deflect the first and second ramp portions into the cavity allowing the bump stop to rotate past the at least one generally elongated torque limiting flex ramp thereby setting a torque limit the tool must overcome to move.

\* \* \* \* \*